United States Patent [19]
Ali

[11] Patent Number: 4,579,828
[45] Date of Patent: Apr. 1, 1986

[54] CLOT ACTIVATOR FOR SERUM SEPARATION TUBES

[75] Inventor: Keramat Ali, Sumter, S.C.

[73] Assignee: Becton, Dickinson and Company, Paramus, N.J.

[21] Appl. No.: 561,753

[22] Filed: Dec. 15, 1983

[51] Int. Cl.[4] .......................... C03C 3/06; G01N 33/86
[52] U.S. Cl. ............................................. 501/12; 65/17; 65/22; 73/64.1; 210/927; 422/73; 422/102; 436/69; 501/39; 501/53
[58] Field of Search ...................... 65/22, 17; 73/64.1; 128/637; 210/927; 422/73, 102; 436/69; 501/12, 53, 54, 39; 423/335

[56] References Cited

U.S. PATENT DOCUMENTS

| | | | |
|---|---|---|---|
| 3,667,909 | 6/1972 | Thomas | 423/325 |
| 4,028,085 | 6/1977 | Thomas | 501/12 X |
| 4,153,739 | 5/1979 | Kessler | 427/2 |
| 4,257,886 | 3/1981 | Kessler | 210/516 |
| 4,402,927 | 9/1983 | von Dardel et al. | 423/335 |

FOREIGN PATENT DOCUMENTS

| | | | |
|---|---|---|---|
| 2453813 | 5/1976 | Fed. Rep. of Germany | 73/64.1 |
| 53-28495 | 3/1978 | Japan | 210/927 |
| 56-125240 | 10/1981 | Japan | 501/54 |

OTHER PUBLICATIONS

Yamane et al, Preparation of a Gel From Metal Alkoxide and its Properties as a Precursor of Oxide Glass, J. Material Sci. 13 (1978) 865–70.

Primary Examiner—Barry S. Richman
Assistant Examiner—Michael S. Gzybowski
Attorney, Agent, or Firm—Robert P. Grindle

[57] ABSTRACT

An improved clot activator system for reducing the clotting time for blood samples in serum separation tubes, and the like, as well as increasing the degree of clotting, while at the same time, reducing the cost of production. This is achieved by the addition of glass pieces to the tube which pieces are formed in a particular way by a sol-gel process. The particles are pieces of glass, and are a porous substantially rigid amorphous inorganic sponge with substantial reactive surfaces. When a blood sample is introduced into a serum separation tube containing such pieces, the blood enters the interstices of the pieces causing fragmentation thereof, which fragmentation causes sound and shock waves which, in turn, enhance the clotting of the blood.

14 Claims, 1 Drawing Figure

CLOT ACTIVATOR FOR SERUM SEPARATION TUBES

BACKGROUND AND STATEMENT OF THE INVENTION

This invention relates to a procedure, and a product obtained from that procedure, for increasing the clot activation properties of serum separation tubes once a blood sample has been introduced into the tube. More particularly, this invention relates to a product easily produced separately from such a blood sample collection tube, and which may be easily introduced in a mass production line into a plurality of such tubes, and which product has the effect of increasing the degree of clot activation of the blood sample introduced, as well as reducing the clotting time thereof. More particularly, this invention relates to the development of a particular kind of glass particle or piece from a sol-gel process, which particles or pieces of glass are extremely porous, having a sponge-like rigid amorphous body. The pieces of glass, because of the porous property thereof, fragments upon contact with a blood sample introduced into a serum separation tube containing such particles or pieces, because the blood, by capillary action, enters the interstices of the pieces or particles and causes them to fragment. This fragmentation causes sound and shock waves throughout the blood sample. The sound and shock waves increase the degree of clotting and decrease, simultaneously, the clotting time of the sample.

The length of time required for blood collected in a blood collection assembly to clot after it is introduced into the assembly is dependent upon a number of interrelated factors. One of the factors which increases the rate of clot formation is exposure of the blood to "siliceous" materials such as glass, silica, kaolin, bentonite or diatomaceous earth. Therefore, it is important that the exposure of the blood sample to the presence of a silica in a sample containing tube be as uniform and rapid as possible.

Representative prior art patents which teach, among other things, silica coatings in blood collection tubes, such as serum separation tubes, include U.S. Pat. Nos. 4,153,739 and 4,257,886. The '739 patent teaches a clot activating film 24 with the film being formed of one percent by weight polyvinyl pyrrolidone and one percent by weight silica added to isopropanol. In substitution for polyvinyl pyrrolidone, polyethylene oxide may be used. The '886 patent teaches, on the other hand, a water-soluble clot activating coating 36 wherein the coating is comprised of an admixture of polyvinyl pyrrolidone or polyethylene oxide with clot activating particles such as silica in a solvent such as isopropanol. In both cases the source of the silica is fine silica particles. A further teaching of coatings which provide an enhancement of clot activation is in co-pending U.S. application Ser. No. 375,635 filed May 6, 1982.

While the methods taught in the two patents noted above, as well as the co-pending application, have proved satisfactory in the sense that they produce coatings on substrates such as serum separation tubes, which coatings contain silica for clot activation, all of these approaches require adherance to certain rigid production techniques in order to provide proper coating on the inside of relatively small blood collection tubes. These coatings must be uniform and contain the proper ratio of the individual components in the coatings in order to provide the proper and accurate test results, subsequently, in a clinical laboratory testing the blood specimen contained in the containers.

With this invention, by contrast, an extremely simple approach is provided in the sense that the blood clot activator for such blood collection sample tubes may be produced separately in a simple sol-gel process. No coating procedures are required. A particular kind of glass piece or particle is produced by the sol-gel process of this invention which pieces and/or particles may be introduced in a production line procedure by being simply dropped into the individual tubes, rather than going through a coating procedure. The pieces are, for want of a better word, comprised of an imperfect glass. That is, the pieces are comprised of an amorphous porous glass much in the same form as a sponge, although being relatively rigid. Thus, when blood is introduced into a blood collection tube containing the amorphous glass pieces or particles of the invention, the blood passes into the interstices or pores of the glass of the invention and shatters it. This shattering causes shock waves and sound, both of which properties act to increase the rapidity of clot activation in the blood sample, as well as increasing the degree of clot activation.

In considering generally the conditions for carrying out the process of this invention, ethylsilicate is dissolved in ethyl alcohol in a ratio of 1:1 by volume and hydrolyzed by the addition of an acid or a base such as ammonia, acetic acid, sulphuric acid or hydrochloric acid. Preferably, 1–2% 6N hydrochloric acid is added in the presence of less than a stoichiometric amount of water according to the reaction;

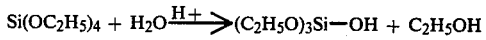

The ethylsilicate is partially hydrolyzed and is, thereafter, polymerized at room temperature to form a gel, according to the following reaction;

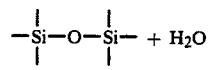

This gel is the resulting silica glass in a semi-solid form. The semi-solid form is simply allowed to dry at room temperature thereafter for two to three hours, followed by heating at a relatively low temperature to drive off the ethyl alcohol, the water and excess hydrochloric acid, leaving the small pores originally formed in the formed glass contained in the glass. It is, in effect, an unfinished amorphous-like or rigid sponge-like inorganic material in the form of relatively large pieces or particles of the material, which may then be introduced into the blood collection tubes.

With the foregoing and additional objects in view, this invention will now be described in more detail, and other objects and advantages thereof will be apparent from the following description, the accompanying drawing, and the appended claims.

DETAILED DESCRIPTION OF THE INVENTION

Figure 1:
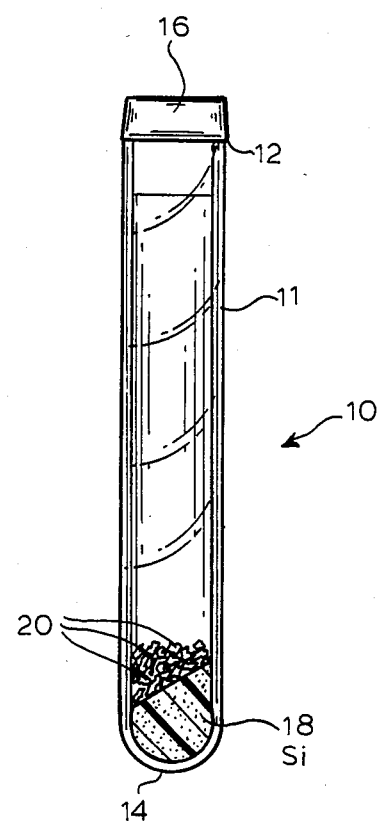
FIG. 1 is a longitudinal sectional view of a serum separation tube assembly illustrating the invention.

Referring to the drawing, a serum separation tube assembly is designated generally 10 having a tube 11, preferably of glass, with a closed end 14 and an open end 12. An elastomeric stopper 16 is disposed in the open end 12 for maintaining an evacuated tube assembly for receiving a blood sample, for example. The elastomeric stopper 16 includes an upper and a lower well, not shown, for easing the passage of a cannula therethrough for introducing a blood sample into tube 11. A silicon based gel material 18, such as that described in U.S. Pat. No. 3,920,549, may then be positioned in the bottom of tube 11 as shown in the FIGURE. As will be understood by practitioners-in-the-art, the gel material 18 is a thixotropic material which, under the action of centrifugal force, moves upward in tube 11 to divide the heavier and lighter fractions of an introduced blood sample.

In accordance with this invention, a plurality of particles or pieces 20 of the sol-gel process of the invention are introduced into tube 11. Thus, when a blood sample is first introduced into tube 11, the blood enters the interstices of the individual particles 20 causing them to shatter and produce both sound and shock waves throughout the blood sample. This enhances the rapidity of the formation of clotting prior to separation of the blood phases under centrifugation.

In considering, generally, the conditions for carrying out the invention, approximately 100 milligrams of the glass particles or pieces of the invention obtained from the sol-gel process of the invention are placed in a serum separation tube of a size which will hold approximately 9.5 milliliters of blood.

As purely illustrative of the process of the invention herein, a specific example was carried out for imparting a clot activation property to a serum separation tube wherein the properties of clot activation obtained for the tube were produced separately for subsequent introduction into such serum separation tubes. It is to be understood, however, that this example is being presented with the understanding that it has no limiting character on the broad disclosure of the invention as generally set forth herein and as directed to men skilled in the art.

EXAMPLE I

Preparation of Porous Silica Glass of the Invention 10.4 grams (0.05 mole) of ethylsilicate were dissolved in 10 ml. of ethyl alcohol. To this mixture was added 0.20 ml. of 6N hydrochloric acid, and the mixture was allowed to sit for ten to fifteen minutes in order to initiate partial hydrolysis of the ethylsilicate.

To the partially hydrolyzed ethylsilicate, was added slowly 5.0 ml. of water. The mixture was then left at room temperature while stirring with a magnetic stirrer in order to polymerize the ethylsilicate. During this stirring procedure, the reaction mixture became viscous. Ultimately, the reaction mixture solidified to a relatively clear glass form. This resulting glass was dried in ambient for 2-3 hours. Finally, the glass was dried at a relatively low elevated temperature level of about 110°-120° C. for one hour. During this mildly elevated temperature drying procedure, the glass broke down to small particles or pieces of the invention in sizes within the range of between about 2 mm.×2 mm. and 2 mm.×10 mm.

As discussed above, and if desired, the serum separation tubes may have introduced into them a thixotropic gel material, as described in the aforementioned U.S. Pat. Nos. 4,257,886 and 4,153,739, so as to produce blood serum separation tubes. Other subsequent processing steps may also be applied, depending upon the ultimate testing applications for which the resulting product is to be used. Subsequent to these processing procedures, then the glass produced in accordance with the example shown above and in accordance with this invention may be introduced into the serum separation tubes on a production line basis prior to the simultaneous sealing with the stopper and the application of a vacuum.

As further illustrative of the results achieved with the process and product of this invention, one may note the comparative results below in Example II between serum separation tubes in which a silica coating was applied to the internal surfaces of the blood collection tubes in accordance with the patents noted above, and separate serum separation tubes having the sol-gel process glass of the invention introduced, in which the glass quantity was approximately 100 mg. In this test procedure, the tubes are Number 6510 VACUTAINER brand SST tubes, a product of Becton Dickinson and Company, which tubes hold 9.5 ml. of blood.

EXAMPLE II

| BLOOD SAMPLES (Average of 10 Samples) | CLOTTING TIME IN REGULAR SST TUBES WITH SILICA COATING | CLOTTING TIME IN SST TUBES WITH SILICA GLASS ACTIVATOR |
| --- | --- | --- |
| #1 | 8 Minutes | 8 Minutes |
| #2 | 9 Minutes | 7 Minutes |
| #3 | 5 Minutes | 4 Minutes |

As can be seen from Example II, with the introduction of the separate glass particles or pieces of the invention, in accordance herewith, there is a substantial increase in the speed of clotting of the samples with most samples. With respect to sample 1 it will be noted that the clotting time is at least equal to that produced by previous coating procedures. However, such coating procedures are much more costly in the sense that much more difficult controls must be provided in order to produce such coatings internally of relatively small glass containers.

Accordingly, as will be apparent from the foregoing, there is provided, in accordance with this invention, a method for producing an improved clot activating property for blood sample collection tubes not only from the standpoint of increasing the degree and speed of clotting, but also from the standpoint of reducing the cost and difficulty of control procedures necessary for introducing the clot activating property to the tubes involved. Thus, as will be understood by practitioners-in-the-art, the improved products obtained by the invention herein are obtained at reduced costs which reduces the cost of medical testing utilizing the products of the invention.

While the methods and compositions herein disclosed form preferred embodiments of this invention, this invention is not limited to those specific methods and compositions, and changes can be made therein without departing from the scope of the invention which is defined in the appended claims.

What is claimed is:

1. A process for producing and utilizing a blood clot activator material, characterized by the steps of
   (a) forming a mixture by admixing ethylsilicate and ethyl alcohol;
   (b) initiating hydrolysis of the mixture formed from said forming step by adding a reactant selected from the group consisting of ammonia, acetic acid, sulphuric acid, and hydrochloric acid;
   (c) partially hydrolyzing said mixture from said adding step, by introducing therein less than a stoichiometric quantity of water;
   (d) maintaining in a first maintaining step said mixture from said partial hydrolysis step at room temperature while stirring for a period of time sufficient to polymerize said ethylsilicate into a solidified form of glass;
   (e) maintaining in a second maintaining step said solidified glass obtained from said first maintaining step at room temperature for a period of time sufficient to dry said solidified glass;
   (f) maintaining in a third maintaining step said solidified glass from said second maintaining step at an elevated temperature within the range of between about 110° C. and 120° C. to break down said solidified glass into small pieces; and
   (g) introducing a quantity of said small pieces from said third maintaining step into each of a plurality of blood collection containers;
   (h) whereby blood samples subsequently introduced into said plurality of blood collection containers are caused to clot.

2. The process of claim 1, further characterized by
   (a) said forming step being carried out with a mixture of ethylsilicate and ethyl alcohol in the ratio of 1:1 by volume.

3. The process of claim 1, further characterized by
   (a) said second maintaining step being carried out for within the range of between about 2 and 3 hours.

4. The process of claim 1, further characterized by
   (a) said small pieces from said third maintaining step being of a size within the range of between about 2 millimeters by 2 millimeters and 2 millimeters by 10 millimeters.

5. In a blood sample collection device having means for activating blood clotting properties comprising
   (a) a container having an opening;
   (b) a closure for said opening;
   (c) a quantity of an amorphous rigid porous glass in said container;
   wherein the improvement comprises said glass being amorphous porous imperfect glass material obtained by the process of
   (d) forming a mixture by admixing ethylsilicate and ethyl alcohol;
   (e) initiating hydrolysis of the mixture formed from said forming step by adding a reactant selected from the group consisting of ammonia, acetic acid, sulphuric acid and hydrochloric acid;
   (f) partially hydrolyzing said mixture from said adding step, by introducing therein less than a stoichiometric quantity of water;
   (g) maintaining in a first maintaining step said mixture from said partial hydrolysis step at room temperature while stirring for a period of time sufficient to polymerize said ethylsilicate into a solidified form of glass;
   (h) maintaining in a second maintaining step said solidified glass obtained from said first maintaining step at room temperature for a period of time sufficient to dry said solidified glass;
   (i) maintaining in a third maintaining step said solidified glass from said second maintaining step at an elevated temperature within the range of between about 110° C. and 120° C. to break down said solidified glass into small pieces; and
   (j) introducing a quantity of said small pieces from said third maintaining step into said container opening;
   (k) whereby a blood sample subsequently introduced into said container is caused to clot.

6. The device of claim 5, further characterized by
   (a) said container is an evacuated container.

7. The device of claim 5, further characterized by
   (a) said forming step being carried out with a mixture of ethylsilicate and ethyl alcohol in the ratio of 1:1 by volume.

8. The device of claim 5, further characterized by
   (a) said second maintaining step being carried out for within the range of between about 2 and 3 hours.

9. The device of claim 5, further characterized by
   (a) said small pieces from said third maintaining step being of a size within the range of between about 2 millimeters by 2 millimeters and 2 millimeters by 10 millimeters.

10. The device of claim 5, further characterized by
    (a) said container is an evacuated serum separation tube having an open end and a closed end; and
    (b) a thixotropic gel positioned in the closed end of said tube prior to said introducing step.

11. An amorphous porous imperfect glass material in the form of pieces for introduction into blood sample collection devices for enhancing clot activation of blood samples subsequently introduced into such devices, said glass pieces obtained by the process of
    (a) forming a mixture by admixing ethylsilicate and ethyl alcohol;
    (b) initiating hydrolysis of the mixture formed from said forming step by adding a reactant selected from the group consisting of ammonia, acetic acid, sulphuric acid and hydrochloric acid;
    (c) partially hydrolyzing said mixture from said adding step, by introducing therein less than a stoichiometric quantity of water;
    (d) maintaining in a first maintaining step said mixture from said partial hydrolysis step at room temperature while stirring for a period of time sufficient to polymerize said ethylsilicate into a solidified form of glass;
    (e) maintaining in a second maintaining step said solidified glass obtained from said first maintaining step at room temperature for a period of time sufficient to dry said solidified glass;
    (f) maintaining in a third maintaining step said solidified glass from said second maintaining step at an elevated temperature within the range of between about 110° C. and 120° C. to break down said solidified glass into small pieces.

12. The blood clot activator material of claim 11, further characterized by
    (a) said forming step being carried out with a mixture of ethylsilicate and ethyl alcohol in the ratio of 1:1 by volume.

13. The blood clot activator material of claim 11, further characterized by (a) said second maintaining step being carried out for within the range of between about 2 and 3 hours.

14. The blood clot activator material of claim 11, further characterized by (a) said small pieces from said third maintaining step being of a size within the range of between about 2 millimeters by 2 millimeters and 2 millimeters by 10 millimeters.

* * * * *